United States Patent [19]

Mishima et al.

[11] Patent Number: 5,187,310

[45] Date of Patent: Feb. 16, 1993

[54] ORGANIC SILICON COMPOUND, METHOD OF ITS PRODUCTION, AND PHOTORECEPTOR FOR ELECTROPHOTOGRAPHY INCORPORATING IT

[75] Inventors: Masayuki Mishima; Harumasa Yamasaki; Takashi Matsuse; Tadashi Sakuma; Hiroyasu Togashi, all of Wakayama, Japan

[73] Assignee: Kao Corporation, Tokyo, Japan

[21] Appl. No.: 666,204

[22] Filed: Mar. 7, 1991

[30] Foreign Application Priority Data

Mar. 14, 1990 [JP] Japan .................................. 2-64616
Mar. 14, 1990 [JP] Japan .................................. 2-64617
Mar. 16, 1990 [JP] Japan .................................. 2-65725

[51] Int. Cl.$^5$ ............................................. C07F 7/10
[52] U.S. Cl. ................................. 556/413; 250/214.1
[58] Field of Search ........................................ 556/413

[56] References Cited

U.S. PATENT DOCUMENTS

| | | | |
|---|---|---|---|
| 2,960,517 | 11/1960 | Schnabel | 260/448.2 |
| 3,171,851 | 3/1965 | Pepe | 556/413 |
| 3,308,144 | 3/1967 | Napoli | 556/413 |
| 3,344,070 | 9/1967 | Schiefer et al. | 556/413 X |
| 3,350,311 | 10/1967 | Napoli | 556/413 X |
| 3,697,429 | 3/1972 | Goldman et al. | 556/413 X |

FOREIGN PATENT DOCUMENTS 0332921 9/1989 European Pat. Off. .
53-27033 3/1978 Japan .
56-35140 4/1981 Japan .

OTHER PUBLICATIONS

World Patent Index (Online), Accession No. 88-088 429 Derwent Publications Ltd., London.

Jones et al, J. Amer. Chem. Soc., 94(13), pp. 4595-4599 (1972).

Primary Examiner—Paul F. Shaver
Attorney, Agent, or Firm—Birch, Stewart, Kolasch & Birch

[57] ABSTRACT

A compound represented by the formula (1):

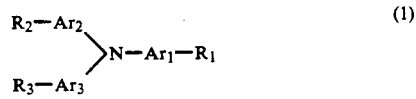

wherein $Ar_1$ represents an arylene group; $Ar_2$ and $Ar_3$ independently represent an aryl group or an arylene group; $R_2$ and $R_3$, which may be identical or not, independently represent a hydrogen atom or an alkyl group having a carbon number of 4 or less, or $R_2$ and $R_3$ both represent —$SiR_4R_5R_6$ ($R_4$, $R_5$ and $R_6$, which may be identical or not, independently represent an alkyl group, aralkyl group or aryl group which may be substituted);

$R_1$ represents —$SiR_7R_8R_9$ ($R_7$, $R_8$ and $R_9$, which may be identical or not, independently represent an alkyl group, cycloalkyl group, aralkyl group or aryl group which may be substituted, or none (only in the case where $R_2$ and $R_3$ represent —$SiR_4R_5R_6$), one or two of $R_7$, $R_8$ and $R_9$ represent the following:

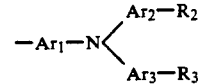

wherein $Ar_1$, $Ar_2$, $Ar_3$, $R_2$ and $R_3$ have the same definitions as above), a method of its production and a photoreceptor for electrophotography incorporating it as a change transport material. The photoreceptor is very excellent in sensitivity and durability.

21 Claims, No Drawings

ORGANIC SILICON COMPOUND, METHOD OF ITS PRODUCTION, AND PHOTORECEPTOR FOR ELECTROPHOTOGRAPHY INCORPORATING IT

BACKGROUND OF THE INVENTION

1. Field of the Invention

The present invention relates to a silicon-containing triarylamine compound, a method of its production and a high-sensitivity high-durability photoreceptor for electrophotography incorporating said silicon-containing triarylamine compound as the charge transport material.

2. Description of the Prior Art

In recent years, there have been noticeable improvements in copying machines and printers based on electrophotography. A wide variety of new models of different shapes, types and functions have been developed according to uses, and various photoreceptors for such new models have been developed accordingly.

Traditionally, photoreceptors for electrophotography have been based mainly on an inorganic compound from the viewpoint of its sensitivity and durability. Examples of such inorganic compounds include zinc oxide, cadmium sulfide and selenium. However, these substances are often toxic, thus posing problems of disposal and environmental pollution. In addition, when using selenium, which offers good sensitivity, it is necessary to form a thin film on a conductive substrate by vacuum deposition, etc., which results in poor productivity and increased production cost.

Amorphous silicon has recently drawn much attention as an inorganic photoreceptor free of environmental pollution, and research and development activities are in progress. However, the use of the plasma CVD method for film formation results in extremely poor productivity and increased photoreceptor production cost and running cost, though excellent sensitivity is obtained.

On the other hand, organic photoreceptors have the advantage of being free of environmental pollution since they are burnable, many of which permit easy mass production since they are coatable for thin films. These aspects are advantageous in that significant cost reduction is possible and a wide range of shapes can be obtained according to uses. It should be noted, however, that organic photoreceptors involve some problems to be solved as to sensitivity and durability; there are strong demands for the development of an organic photoreceptor with high sensitivity and high durability.

Various methods have been proposed to improve the sensitivity of organic photoreceptor, but the current main stream uses photoreceptors having a double-layered photoconductive structure in which functions are allotted to a charge generation layer and a charge transport layer. For example, the charge generated in the charge generation layer in response to exposure is injected to the charge transport layer, through which it is transported to the surface of the photoreceptor, where the surface charge is neutralized and an electrostatic latent image is formed thereon. Thus, in the double-layered photoconductive structure type in comparison with the single-layered structure type, the generated charge is less likely to be trapped, and the charge can be more efficiently transported to the surface of the photoreceptor (U.S. Pat. No. 2,803,541).

As the organic charge generation material for the charge generation layer, a compound which absorbs the energy of the irradiated light and efficiently generates a charge is selected and used. Examples of such compounds include an azo pigment (Japanese Patent Publication Open to Public Inspection No. 14967/1979), a metal-free phthalocyanine pigment (Japanese Patent Publication Open to Public Inspection No. 143346/1985), a metallophthalocyanine pigment (Japanese Patent Publication Open to Public Inspection No. 16538/1975) and a squarylium salt (Japanese Patent Publication Open to Public Inspection No. 27033/1978).

As the charge transport material for the charge transport layer, it is necessary to select a compound which offers a high efficiency of charge injection from the charge generation layer and a high charge mobility in the charge transport layer. To meet these requirements, a compound having a low ionization potential or a compound which easily releases a cationic radical is selected. Examples of such compounds proposed include a triarylamine derivative (Japanese Patent Publication Open to Public Inspection No. 47260/1978), a hydrazone derivative (Japanese Patent Publication Open to Public Inspection No. 101844/1982), an oxadiazole derivative (Japanese Patent Examined Publication No. 5466/1959), a pyrazoline derivative (Japanese Patent Examined Publication No. 4188/1977), a stilbene derivative (Japanese Patent Publication Open to Public Inspection No. 198043/1983), a triphenylmethane derivative (Japanese Patent Examined Publication No. 555/1970), and a 1,3-butadiene derivative (Japanese Patent Publication Open to Public Inspection No. 287257/1987).

As stated above, however, these organic photoreceptors are lower than inorganic photoreceptors in charge mobility, and their sensitivity remains unsatisfactory.

Also, in a series of electrophotographic processes of charging, exposure, development, toner transfer and discharging, the photoreceptor is subject to extremely severe conditions and its ozone resistance and abrasion resistance are of great concern, although improvements in these durability properties are demanded, no satisfactory photoreceptors have been developed.

Above all, triarylamine has been investigated for a large number of derivatives, including monotriarylamine (Japanese Patent Publication Open to Public Inspection Nos. 195254/1982, 118147/1989 and 118142/1989), bis(diarylamino)benzene (Japanese Patent Publication Open to Public Inspection Nos. 144250/1980, 118144/1989 and 118146/1989) and bistriarylamine (Japanese Patent Publication Open to Public Inspection Nos. 27033/1978, 35140/1981, 52756/1981 and 142647/1989).

However, monotriarylamine has drawbacks, including insufficient charge mobility and a lack of stability, though it is generally easy to synthesize. As for bis(diarylamino)benzene and bistriarylamine, they have drawbacks such as a lack of stability and difficult synthesis, though they offer a fair level of charge mobility. Also, these triarylamine derivatives all have been suggested to pose a problem regarding a lack of compatibility with binder resin.

As stated above, conventional organic photoreceptors such as triarylamine derivatives have many drawbacks, and there are strong demands for improvements to overcome these drawbacks in the relevant technical field.

It should be noted that a silicon-containing triarylamine compound which is similar to the present invention is disclosed in U.S. Pat. No. 2,960,517, but it is a monosilyltriarylamine compound and is unsuitable for use as a charge transport material for photoreceptor for electrophotography because it is liquid at normal temperature. In addition, it is produced by reaction of a bromophenylalkylsilane compound and an alkali metal salt of amine, and these starting materials are not easily available and this reaction requires severe conditions both for reaction temperature and for reaction time.

SUMMARY OF THE INVENTION

It is an object of the present invention to provide a novel compound which has excellent charge mobility and excellent stability, which is compatible with binder resin and which serves well as a charge transport material, whereby the problems described above are solved.

It is still another object of the present invention to provide a method of producing said novel compound.

It is still another object of the present invention to provide a high-sensitivity high-durability photoreceptor for electrophotography which incorporates said novel compound as the charge transport material.

With the aim of solving the problems described above, the present inventors made intensive investigations and developed the present invention.

Accordingly, a mode of the present invention relates to a silicon-containing triarylamine compound represented by the formula (1):

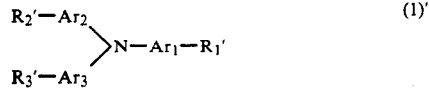

wherein $Ar_1$ represents an arylene group; $Ar_2$ and $Ar_3$ independently represent an aryl group or an arylene group; $R_2$ and $R_3$, which may be identical or not, independently represent a hydrogen atom or an alkyl group having a carbon number of 4 or less, or $R_2$ and $R_3$ both represent —$SiR_4R_5R_6$ ($R_4$, $R_5$ and $R_6$, which may be identical or not, independently represent an alkyl group, aralkyl group or aryl group which may be substituted);
$R_1$ represents —$SiR_7R_8R_9$ ($R_7$, $R_8$ and $R_9$, which may be identical or not, independently represent an alkyl group, cycloalkyl group, aralkyl group or aryl group which may be substituted, or none (only in the case where $R_2$ and $R_3$ represent —$SiR_4R_5R_6$), one or two of $R_7$, $R_8$ and $R_9$ represent the following:

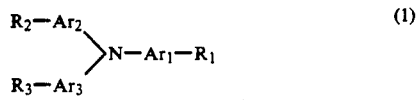

wherein $Ar_1$, $Ar_2$, $Ar_3$, $R_2$ and $R_3$ have the same definitions as above).

Another mode of the present invention relates to a method of producing a silicon-containing triarylamine compound characterized by lithionation of a halogenated triarylamine compound represented by the formula (1)' with an organic lithium reagent, followed by reaction with a silane compound represented by $X_1SiR_7'R_8'R_9'$ ($X_1$ represents a halogen atom, a methoxy group or an ethoxy group; none, one or two of $R_7'$, $R_8'$ and $R_9'$ represent a halogen atom, a methoxy group or an ethoxy group while the remaining one, two or three, which may be identical or not, represent an alkyl group, cycloalkyl group, aralkyl group or aryl group which may be substituted),

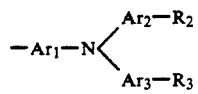

wherein $Ar_1$, $Ar_2$ and $Ar_3$ have the same definitions as above; one or all of $R_1'$, $R_2'$ and $R_3'$ are halogen atoms, and if they are not halogen atoms, $R_1'$ has the same definition as $R_1$, $R_2'$ has the same definition as $R_2$, and $R_3'$ has the same definition as $R_3$.

Still another mode of the present invention relates to a method of producing a silicon-containing triarylamine compound characterized by reaction of a halogenated triarylamine compound of the formula (1)' wherein one or all of $R_1'$, $R_2'$ and $R_3'$ are halogen atoms, with metallic magnesium, followed by reaction with a silane compound represented by $X_1SiR_7'R_8'R_9'$ ($X_1$ represents a halogen atom, a methoxy group, or an ethoxy group; none, one or two of $R_7'$, $R_8'$ and $R_9'$ represent a halogen atom, a methoxy group, or an ethoxy group while the remaining one, two or three, which may be identical or not, represent an alkyl group, cycloalkyl group, aralkyl group or aryl group which may be substituted).

Still yet another mode of the present invention relates to a photoreceptor for electrophotography essentially comprising a conductive substrate and a light-sensitive layer formed thereon characterized by the containment of a silicon-containing triarylamine compound of the present invention in said light-sensitive layer.

The silicon-containing triarylamine compound represented by the formula (1) of the present invention can be specifically represented by the formulas (2) through (4).

A compound represented by the formula (2):

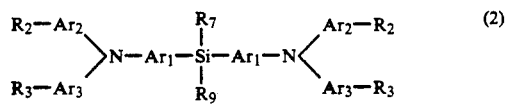

wherein $Ar_1$, $Ar_2$, $Ar_3$, $R_2$, $R_3$, $R_7$ and $R_9$ have the same definitions as above.

A compound represented by the formula (3):

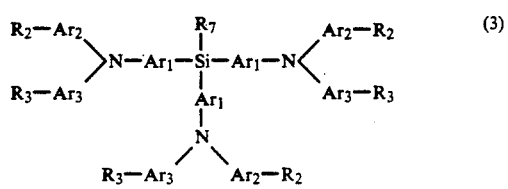

wherein $Ar_1$, $Ar_2$, $Ar_3$, $R_2$, $R_3$ and $R_7$ have the same definitions as above.

A compound represented by the formula (4):

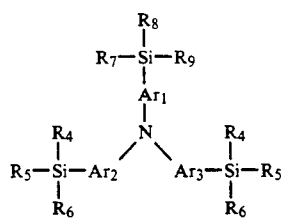

(4)

wherein $Ar_1$, $Ar_2$, $Ar_3$, $R_4$, $R_5$, $R_6$, $R_7$, $R_8$ and $R_9$ have the same definitions as above.

DETAILED DESCRIPTION OF THE INVENTION

With respect to the formulas (1) through (4), $Ar_1$ represents an arylene group, and $Ar_2$ and $Ar_3$ independently represent an aryl group or an arylene group. Examples of the aryl group include phenyl, naphthyl and anthranyl; examples of the arylene group include phenylene, naphthylene and anthranylene.

$R_2$ and $R_3$, which may be identical or not, independently represent a hydrogen atom or an alkyl group having a carbon number of 4 or less, or $R_2$ and $R_3$ both represent —$SiR_4R_5R_6$ ($R_4$, $R_5$ and $R_6$, which may be identical or not, independently represent an alkyl group, aralkyl group or aryl group which may be substituted). Examples of the alkyl group having a carbon number of 4 or less include methyl, ethyl, n-propyl, isopropyl, n-butyl, isobutyl, s-butyl and t-butyl, with preference given to methyl and ethyl groups.

The alkyl group for $R_4$, $R_5$ and $R_6$ is a linear or branched alkyl group having a carbon number of 1 to 4. Examples of such alkyl groups include methyl, ethyl, isopropyl, n-propyl, n-butyl, isobutyl, s-butyl and t-butyl. When $R_4$, $R_5$ and $R_6$ are aralkyl groups, examples of its aryl group moiety include phenyl, naphthyl and anthranyl which may be substituted with an alkyl group, alkoxy group or another substituent; examples of the alkylene group moiety include those having a carbon number of 1 to 4, with preference given to methylene. When $R_4$, $R_5$ and $R_6$ are aryl groups, examples of the aryl group include phenyl, naphthyl and anthranyl which may be substituted with an alkoxy group or another substituent, with preference given to phenyl.

It is preferable that $R_4$, $R_5$ and $R_6$ be identical with each other and be aryl groups or aralkyl groups which may be substituted or alkyl groups having a carbon number of 4 or less. When one or more of $R_4$, $R_5$ and $R_6$ are not identical with the other member(s), or when they are alkyl groups having a carbon number of 5 or more, the compound occurs as a liquid or grease at normal temperature and is thus undesirable for use as a charge transport material.

$R_1$ represents —$SiR_7R_8R_9$ ($R_7$, $R_8$ and $R_9$, which may be identical or not, independently represent an alkyl group, cycloalkyl group, aralkyl group or aryl group which may be substituted, or none (only in the case where $R_2$ and $R_3$ represent —$SiR_4R_5R_6$), one or two of $R_7$, $R_8$ and $R_9$ represent the following:

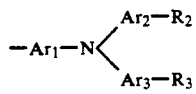

wherein $Ar_1$, $Ar_2$, $Ar_3$, $R_2$ and $R_3$ have the same definitions as above).

Here, when $R_7$, $R_8$ and $R_9$ are alkyl groups, aralkyl groups or aryl groups, they are exemplified by the same groups mentioned for $R_4$, $R_5$ and $R_6$ above. To use a compound of the present invention as a charge transport material, it needs to be solid at normal temperature, and when $R_7$, $R_8$ and $R_9$ are alkyl groups, their carbon number is preferably 1 to 6. When $R_7$, $R_8$ and $R_9$ are cycloalkyl groups, they may have a carbon number of 8 or less, and examples of such cycloalkyl groups include cyclohexyl, cyclopentyl and cyclooctyl.

The silicon-containing triarylamine compounds represented by the formulas (1) through (4) can be produced by one of the methods (A) and (B) described below.

Method (A):

The method in which reaction is carried out between a lithium reagent derived from a halogenated triarylamine compound represented by the formula (1)':

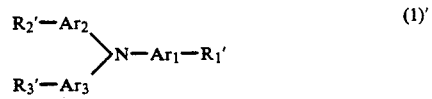

(1)' wherein $Ar_1$, $Ar_2$ and $Ar_3$ have the same definitions as above; one or all of $R_1'$, $R_2'$ and $R_3'$ are halogen atoms; if they are not halogen atoms, $R_1'$ has the same definition as $R_1$, $R_2'$ has the same definition as $R_2$, and $R_3'$ has the same definition as $R_3$, and a silane compound represented by $X_1SiR_7'R_8'R_9'$ ($X_1$ represents a halogen atom, a methoxy group, or an ethoxy group; none, one or two of $R_7'$, $R_8'$ and $R_9'$ independently represent a halogen atom, a methoxy group, or an ethoxy group while the remaining one, two or three, which may be identical or not, independently represent an alkyl group, cycloalkyl group, aralkyl group or aryl group which may be substituted).

Accordingly, in the present invention, a halogenated triarylamine compound represented by the formula (1)' is first dissolved in an ether solvent and lithionated by reaction with an organic lithium reagent. Examples of ether solvents include diethyl ether, diisopropyl ether, di-n-butyl ether, ethylene glycol dimethyl ether, ethylene glycol diethyl ether, diethylene glycol dimethyl ether, diethylene glycol diethyl ether, tetrahydrofuran and dioxane, with preference given to diethyl ether and tetrahydrofuran. To an ether solution of this halogenated triarylamine compound of the formula (1)', an equivalent amount, to the halogen atoms of the above compound, of organic lithium reagent is added dropwise to cause lithionation at a temperature of −50° C. to 100° C. with cooling or heating added as needed. Examples of the organic lithium reagent used include n-butyl lithium, s-butyl lithium, t-butyl lithium, phenyl lithium, methyl lithium and lithium diisopropylamide, with preference given to n-butyl lithium. These reagents are used in dilution in any solvent. To the lithionated solution, a silane compound represented by $X_1SiR_7'R_8'R_9'$ is added dropwise in an amount of 0.9 to 1.1 equivalents at a temperature of 0° to 100° C. with cooling or heating added as needed. After completion of the addition, the mixture is stirred under reflux to the reaction end point. After completion of the reaction, hydrolysis is carried out, and the organic layer is extracted, dried and recrystallized to yield a purified silicon-containing triarylamine compound represented by one of the formula (1) through (4) at high yield.

The halogenated triarylamine compound of the formula (1)' for the present invention can easily be synthesized by any known method. For example, it can be obtained by Ullmann reaction between a diarylamine represented by ($R_2'$—$Ar_2$) ($R_3'$—$Ar_3$)NH ($Ar_2$, $Ar_3$, $R_2'$ and $R_3'$ have the same definitions as above) or a halogenated arylamine represented by $X_1'Ar_1NH_2$ ($Ar_1$ has the same definition as above; $X_1'$ represents a halogen atom) and a p-dihalogenated aryl compound [Berichte, vol. 36, p. 2382 (1903)]. It can also be obtained by directly halogenating a triarylamine compound with a known halogenating agent. There is no limitation on the choice of the halogen atom; any of chlorine atom, bromine atom and iodine atom can be used.

Also, with respect to the silane compound represented by $X_1SiR_7'R_8'R_9'$, $X_1$ is preferably a halogen atom from the viewpoint of reactivity, and when $R_7'$, $R_8'$ and $R_9'$ represent any one of a halogen atom, a methoxy group and an ethoxy group, they are preferably a halogen atom from the viewpoint of reactivity.

The methods for production of the compounds represented by (2) through (4) are described in more detail. First, to prepare the compounds represented by the formula (2), the halogenated triarylamine compound when only $R_1'$ of the formula (1)' is a halogen atom is lithionated with the organic lithium reagent, followed by reaction with a silane compound represented by $X_1SiX_1R_8'R_9'$ (wherein $X_1$ represents a halogen atom, a methoxy group or an ethoxy group, and $R_8'$ and $R_9'$, which may be identical or not, independently represent an alkyl group, cycloalkyl group, aralkyl group or aryl group which may be subustituted).

To prepare the compound of the formula (3), the halogenated triarylamine compound when only $R_1'$ of the formula (1)' is a halogen atom is lithionated with the organic lithium reagent, followed by reaction with a silane compound represented by $X_1SiX_1X_1R_9'$ (wherein $X_1$ represents a halogen atom, a methoxy group or an ethoxy group, and $R_9'$ represents an alkyl group, cycloalkyl group, aralkyl group or aryl group which may be substituted).

And to prepare the compound represented by the formula (4), the halogenated triarylamine compound when $R_1'$, $R_2'$ and $R_3'$ of the formula (1)' are halogen atoms is lithionated with the organic lithium reagent, followed by reaction with a silane compound represented by $X_1SiR_7'R_8'R_9'$ (wherein $X_1$ represents a halogen atom, a methoxy group or an ethoxy group, and $R_7'$, $R_8'$ and $R_9'$, which may be identical or not, independently represent an alkyl group, cycloalkyl group, aralkyl group or aryl group which may be substituted).

Method (B):

The method in which a Grignard reagent derived from a halogenated triarylamine compound represented by the formula (1)' is reacted with a silane compound represented by $X_1SiR_7'R_8'R_9'$.

The Grignard reagent can be obtained by a known method using a halogenated triarylamine compound represented by the formula (1)' and metallic magnesium as starting materials. Specifically, to an ether solvent, metallic magnesium is added in a ratio of 1.0 to 2.0 equivalents of halogen atoms in a halogenated triarylamine compound represented by the formula (1)', followed by the dropwise addition of the halogenated triarylamine compound at a temperature of 0° to 100° C. with cooling or heating added as needed. Examples of the ether solvent used are the same as in the method (A) described above. To the Grignard reagent thus obtained, a silane compound represented by $X_1SiR_7'R_8'R_9'$ is added dropwise in the same manner as the method (A) described above, followed by treatment with a common manner to yield a silicon-containing triarylamine compound represented by any one of the formulas (1) through (4) at high yield.

The methods for production of the compounds represented by (2) through (4) are described in more detail. First, to prepare the compound represented by the formula (2), the halogenated triarylamine compound when only $R_1'$ of the formula (1)' is a halogen atom is reacted with metallic magnesium, followed by reaction with a silane compound represented by $X_1SiX_1R_8'R_9'$ (wherein $X_1$ represents a halogen atom, a methoxy group or an ethoxy group, and $R_8'$ and $R_9'$, which may be identical or not, independently represent an alkyl group, cycloalkyl group, aralkyl group or aryl group which may be substituted).

To prepare the compound of the formula (3), the halogenated triarylamine compound when only $R_1'$ of the formula (1)' is a halogen atom is reacted with metallic magnesium, followed by reaction with a silane compound represented by $X_1SiX_1X_1R_9'$ (wherein $X_1$ represents a halogen atom, a methoxy group or an ethoxy group, and $R_9'$ represents an alkyl group, cycloalkyl group, aralkyl group or aryl group which may be substituted).

And to prepare the compound represented by the formula (4), the halogenated triarylamine compound when $R_1'$, $R_2'$ and $R_3'$ of the formula (1)' are halogen atoms is reacted with metallic magnesium, followed by reaction with a silane compound represented by $X_1SiR_7'R_8'R_9'$ (wherein $X_1$ represents a halogen atom, a methoxy group or an ethoxy group, and $R_7'$, $R_8'$ and $R_9'$, which may be identical or not, independently represent an alkyl group, cycloalkyl group, aralkyl group or aryl group which may be substituted).

The silicon-containing triarylamine compound thus obtained is suitable for use as a charge transport material for a photoreceptor for electrophotography since the silyl group inductive effect results in cation radical stabilization and increased positive charge mobility. As stated above, a silicon-containing triarylamine compound is disclosed in U.S. Pat. No. 2,960,517, but it is a monosilyltriphenylamine compound, essentially different from the silicon-containing triarylamine compound of the present invention, and is unsuitable for use as a material for a photoreceptor for electrophotography because it is liquid at normal temperature. In addition, its production is based on reaction of a bromophenylalkylsilane compound and an alkali metal salt of amine, and these starting materials are not easily available. Furthermore, this reaction requires severe conditions both for reaction temperature and for reaction time. On the other hand, the production method of the present invention uses less expensive materials and permits the obtainment of the desired compound at room temperature at high yield in short time.

Also, these compounds are stable against oxidation by ozone generated in the electrophotographic process, thus yielding a photoreceptor for electrophotography with high sensitivity and high durability.

The silicon-containing triarylamine compound of the present invention is hereinafter described in more detail by means of Example Compounds (5) through (54), but the invention is not limited to them.

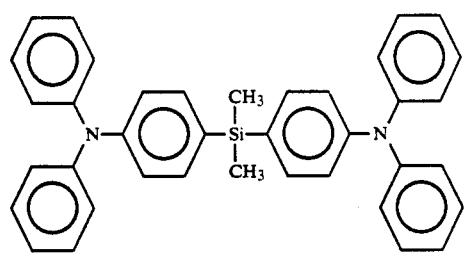
(5)
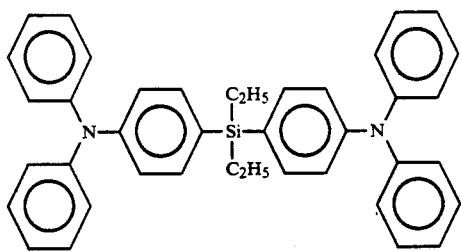
(6)
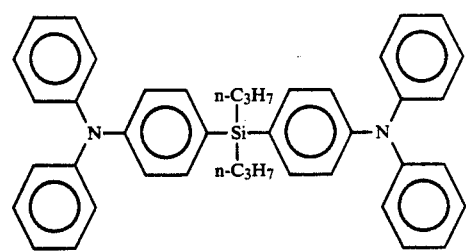
(7)
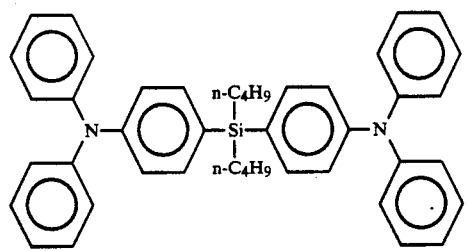
(8)
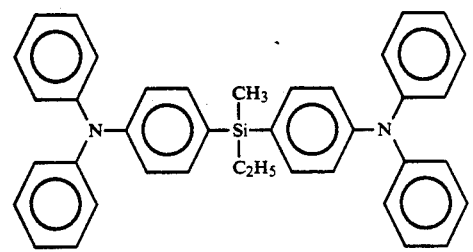
(9)
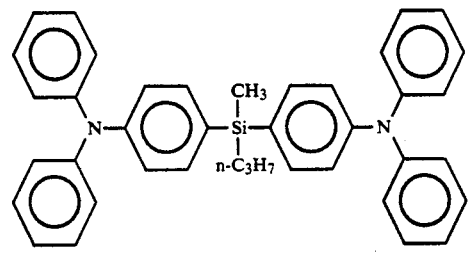
(10)
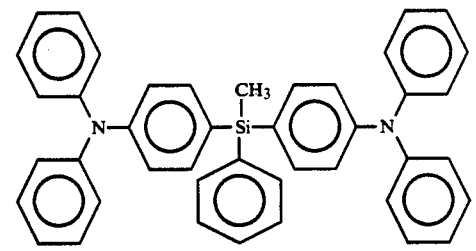
(11)
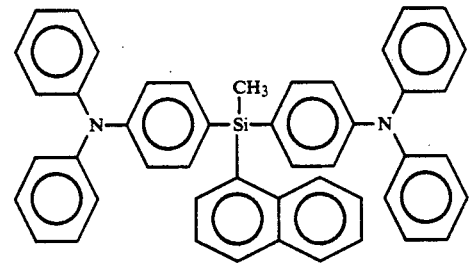
(12)
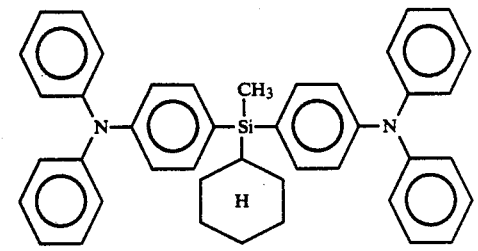
(13)
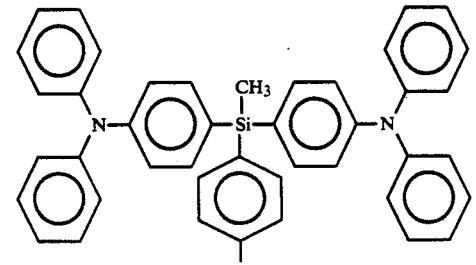
(14)

-continued
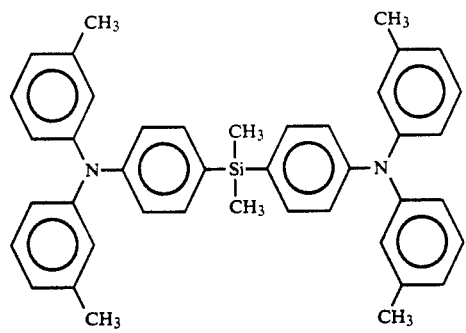 (15)
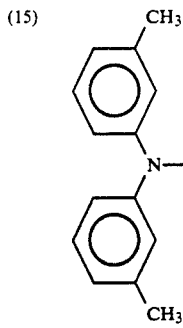 (16)
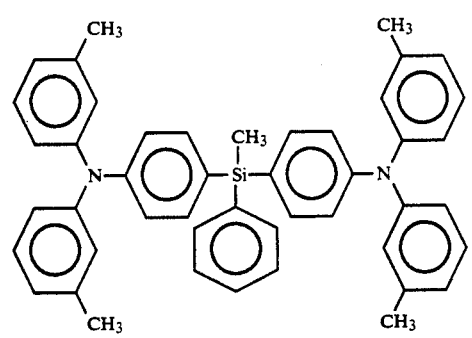 (17)
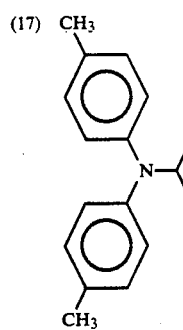 (18)
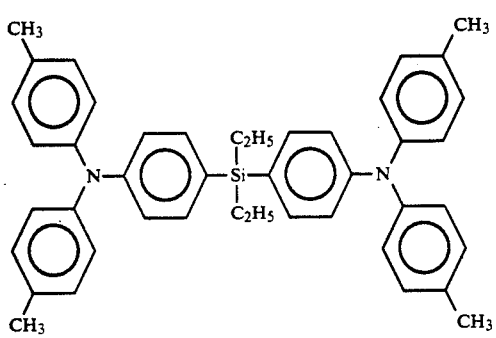 (19)
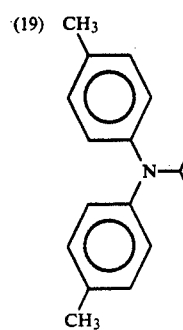 (20)
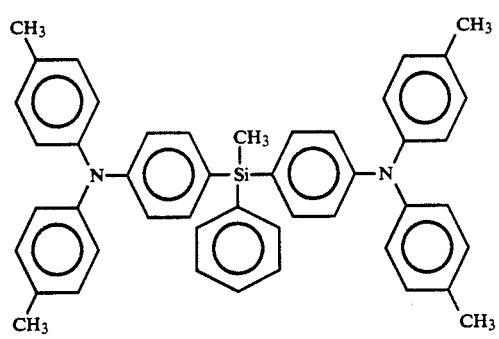 (21)
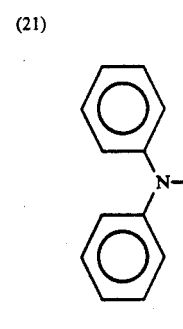 (22)
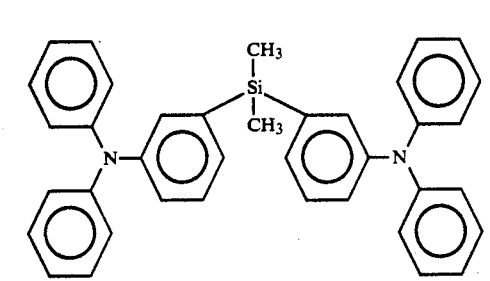 (23)
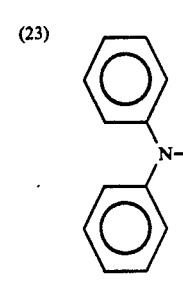 (24)

-continued
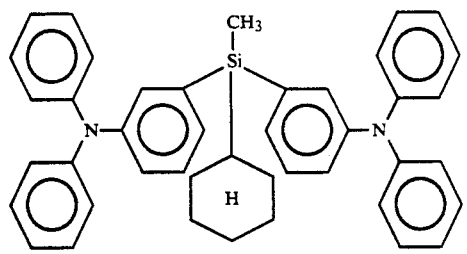
(25)
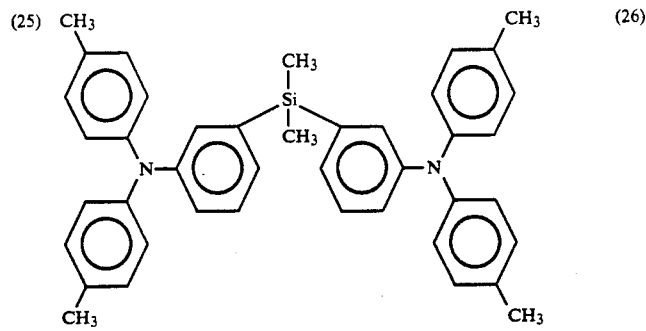
(26)
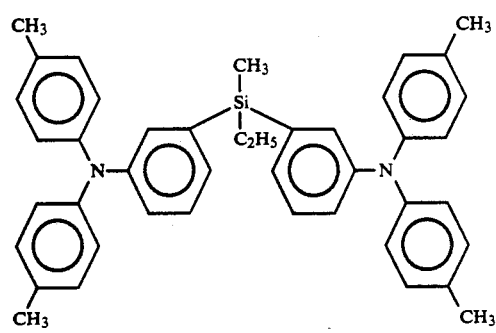
(27)
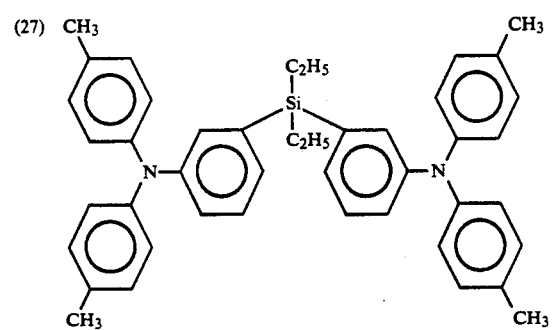
(28)
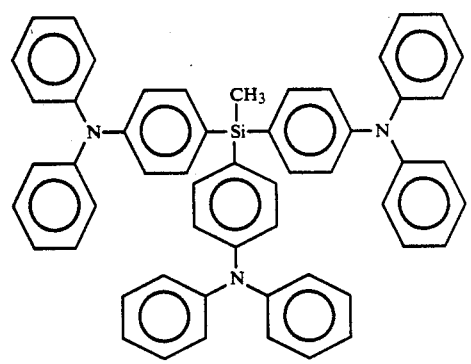
(29)
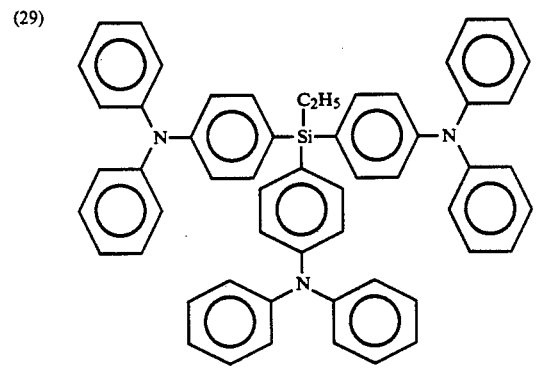
(30)
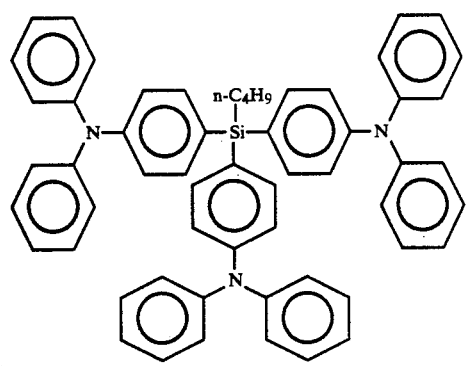
(31)
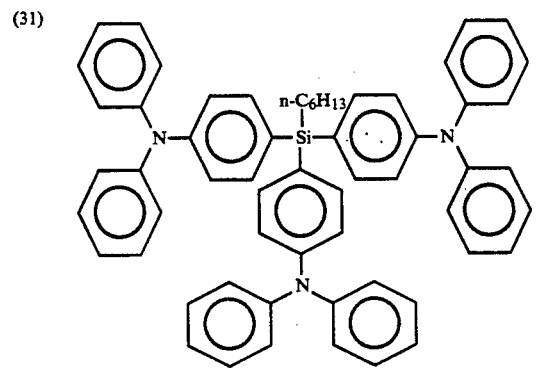
(32)

-continued
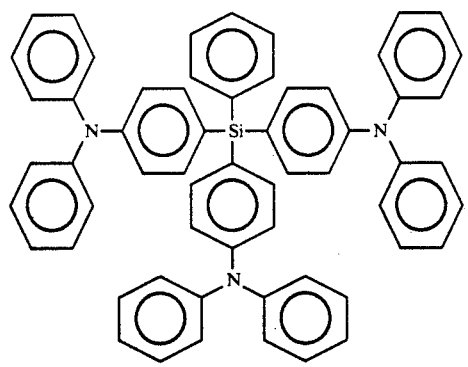
(33)
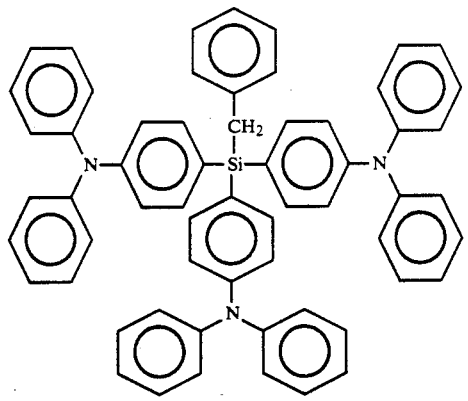
(34)
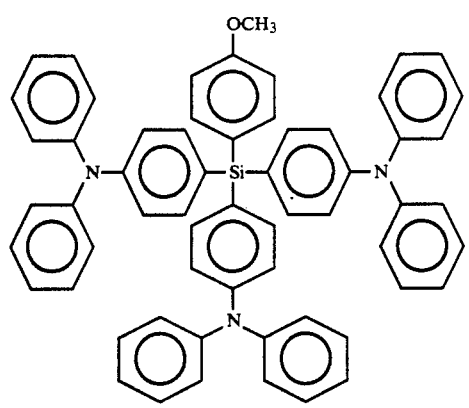
(35)
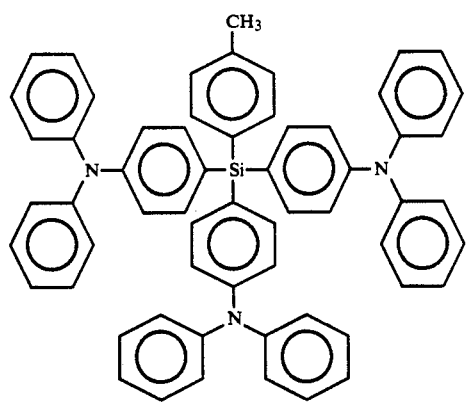
(36)
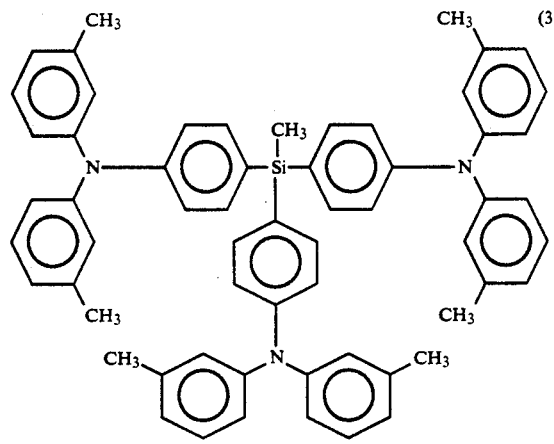
(37)
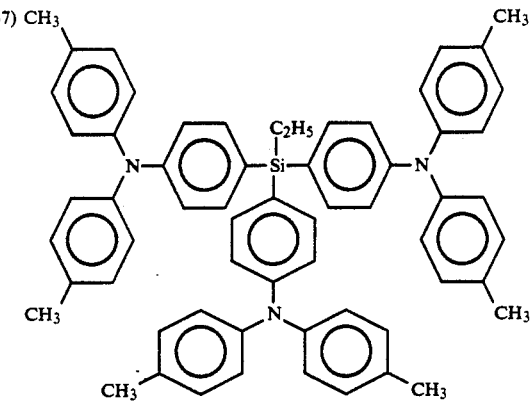
(38)
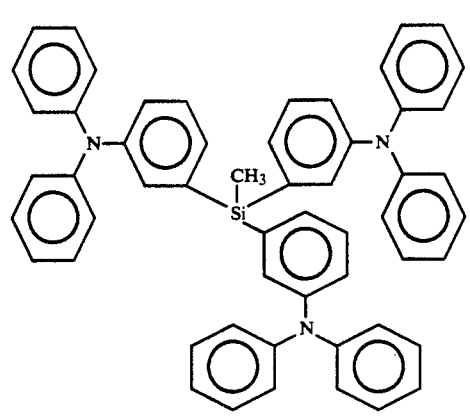
(39)
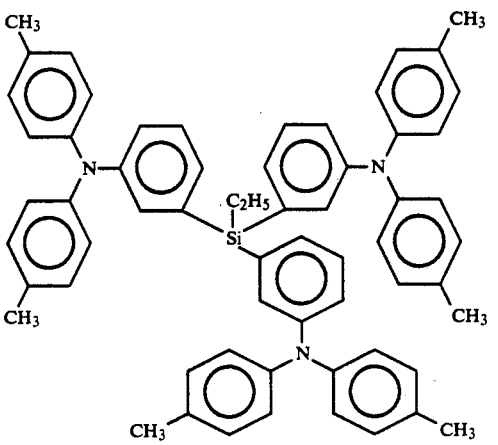
(40)

-continued
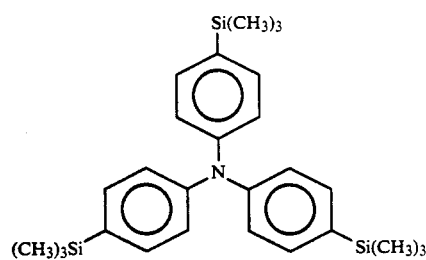 (41)
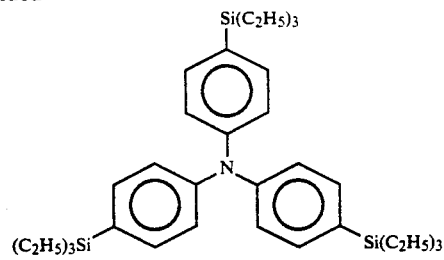 (42)
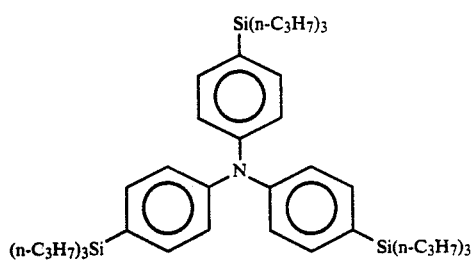 (43)
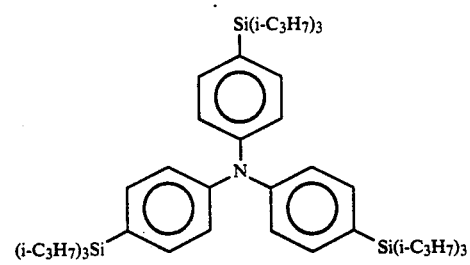 (44)
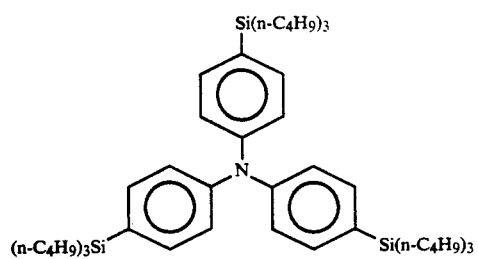 (45)
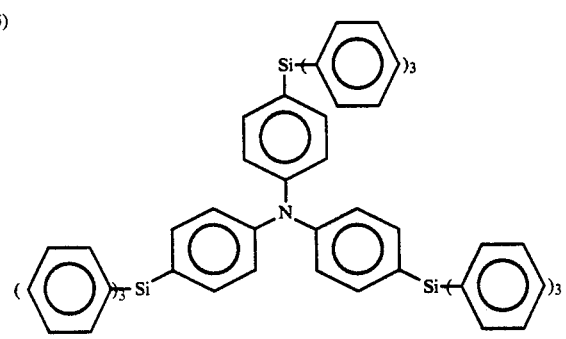 (46)
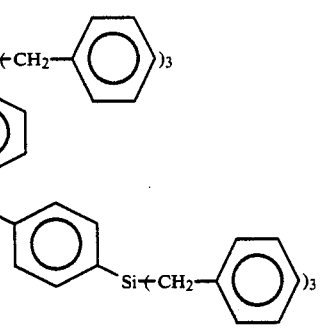 (47)
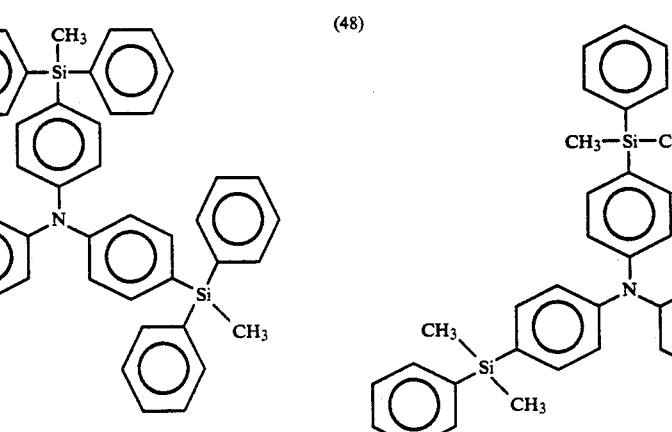 (48)
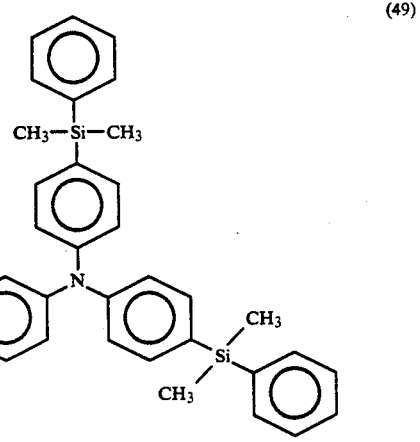 (49)

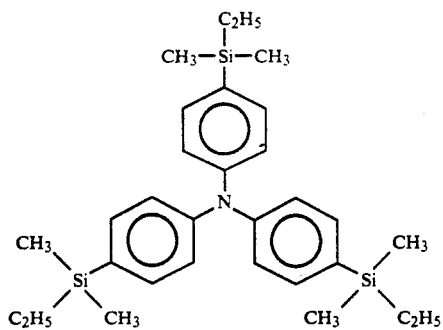 (50)

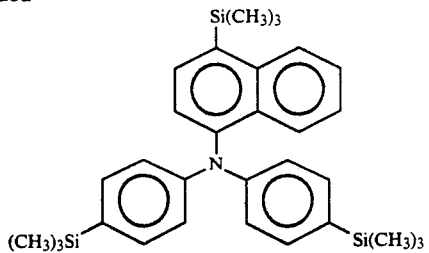 (51)

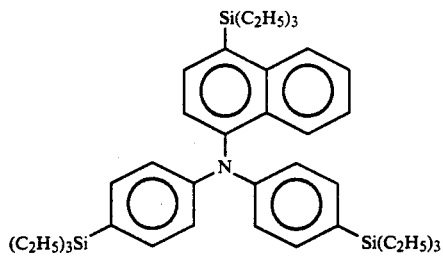 (52)

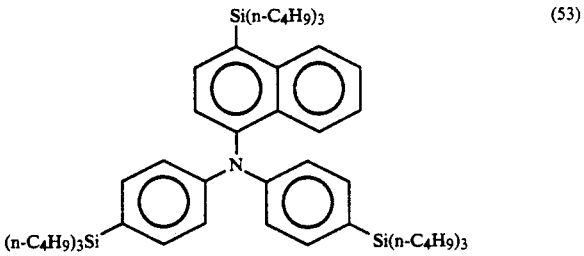 (53)

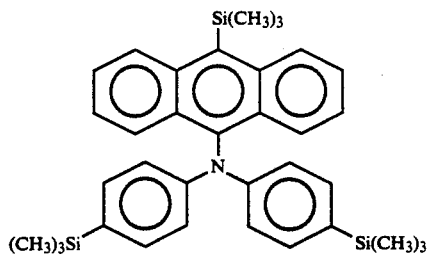 (54)

These compounds are soluble in a large number of solvents, including aromatic solvents such as benzene, toluene, xylene, tetralin and chlorobenzene; halogen solvents such as dichloromethane, chloroform, trichloroethylene and tetrachloroethylene and carbon tetrachloride; ester solvents such as methyl acetate, ethyl acetate, propyl acetate, methyl formate and ethyl formate; ketone solvents such as acetone and methyl ethyl ketone; ether solvents such as diethyl ether, dipropyl ether, dioxane and tetrahydrofuran; alcohol solvents such as methanol, ethanol and isopropyl alcohol; and other solvents such as dimethyl formamide, dimethylacetamide and dimethylsulfoxide.

In the production of a photoreceptor for electrophotography, for example, a charge generation layer and a charge transport layer are formed as thin films on a conductive substrate. Examples of substances which can be used as the conductive substrate include metals such as aluminum and nickel, metal-deposited polymer films and metal-laminated polymer films, which form the conductive substrate in the form of a drum, sheet or belt.

The charge generation layer comprises a charge generation material, and in addition a binder and other additives added as needed, and can be prepared by vacuum deposition, plasma CVD, coating and other methods.

Any organic or inorganic material can be used as the charge generation material with no limitation, as long as it is capable of absorbing the light of a specific wavelength irradiated and of efficiently generating a charge; however, it is preferable to use an organic material since inorganic materials pose problems of environmental pollution and economy as stated above.

Examples of the organic charge generation material include perylene pigment, condensed ring quinone pigment, metal-free phthalocyanine pigment, metallophthalocyanine pigment, bisazo pigment, trisazo pigment, thiapyririum salt, squarylium salt and azulenium pigment, which can be dispersed in binder and used to form a charge generation layer by coating. Examples of the inorganic charge generation material include selenium, selenium alloy, cadmium sulfide, zinc oxide, amorphous silicon and amorphous silicon carbide. Particularly, X-form metal-free phthalocyanine pigment ranks highest in sensitivity in the semiconductor laser wavelength region and dibromoanthanthrone pigment ranks highest in sensitivity in the visible light region.

The thickness of the charge generation layer thus formed is preferably 0.1 to 2.0 μm, more preferably 0.1 to 1.0 μm.

Next, a charge transport layer incorporating a silicon-containing triarylamine compound of the present invention is formed as a thin film on the charge generation layer. The film is formed mainly by coating, specifically, the silicon-containing triarylamine compound of the present invention is dissolved in a solvent in the presence of a binder added as needed, and this solution is coated and then dried on the charge generation layer.

Any solvent can be used with no limitation, as long as it dissolves the compound described above and the binder used as needed and it does not dissolve the charge generation layer.

Any binder used as needed can be used with no limitation, as long as it is an insulating resin. Examples of such binders include condensation polymers such as polycarbonate, polyarylate, polyester and polyamide; addition polymers such as polyethylene, polystyrene, styrene-acrylate copolymer, polyacrylate, polymethacrylate, polyvinylbutyral, polyacrylonitrile, polyacrylamide, acrylonitrile-butadiene copolymer, polyvinyl chloride and vinyl chloride-vinyl acetate copolymer; and others such as polysulfone, polyether sulfone and silicone resin. These binders may be used singly or in combination.

Of these substances, polycarbonate resin, particularly a polycarbonate resin having a repeating unit represented by the formula (55):

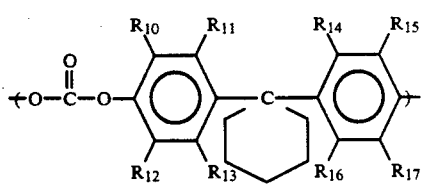

(wherein $R_{10}$, $R_{11}$, $R_{12}$, $R_{13}$, $R_{14}$, $R_{15}$, $R_{16}$ and $R_{17}$, which may be identical or not, independently represent a hydrogen atom, a halogen atom or an alkyl group) (generally referred to as polycarbonate Z resin) is preferred since it offers excellent coating composition storage stability and is less liable to coating defect.

With respect to the formula (55), $R_{10}$ through $R_{17}$, which may be identical or not, independently represent a hydrogen atom, a halogen atom, or an alkyl group, and the halogen atom may be any one of fluorine, chlorine, bromine and iodine atoms, with preference given to chlorine atom. Also, when they represent an alkyl group, it is a linear or branched alkyl group having a carbon number of 1 to 4, and examples include methyl, ethyl, n-propyl, isopropyl and n-butyl, with preference given to methyl.

Such a polycarbonate resin can easily be obtained by a known method such as the reaction of substituted or unsubstituted 1,1-bis(4-hydroxyphenyl)cyclohexane and phosgene (Angewandte Chemie, vol. 68, p. 633 (1956)] or the ester exchange reaction with a diester of carbonic acid such as diphenyl carbonate. A commercially available product produced by Mitsubishi Gas Chemical Co., Inc. or by Teijin Chemicals Co., Ltd. may also be used.

As in a compound having the repeating unit represented by the formula (55) described above, introduction of a cyclohexyl group into the main chain of polycarbonate resin reduces its sliding resistance and makes it possible to increase the toughness without causing a change in its glass transition point. Therefore, a photoreceptor for electrophotography incorporating said polycarbonate Z resin permits minimization of abrasion by toner, paper, cleaning blade, etc. in the electrophotographic process. Examples of the polycarbonate resin having the repeating unit represented by the formula (55) for the present invention are given below [Example Compounds (56) through (60)], with preference given to Example Compound (56) since it is easy to synthesize, but these are not to be construed as limitative on the invention.

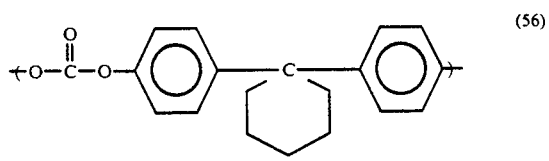

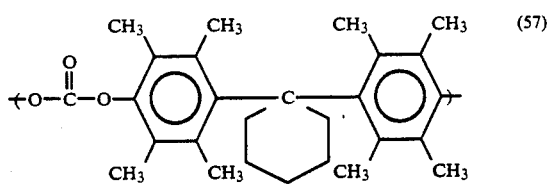

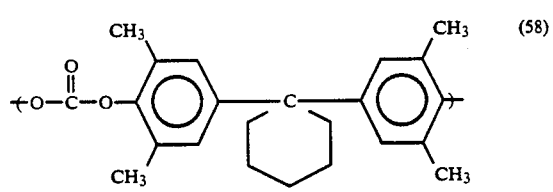

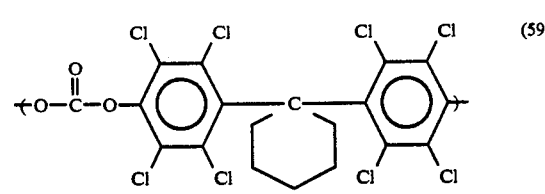

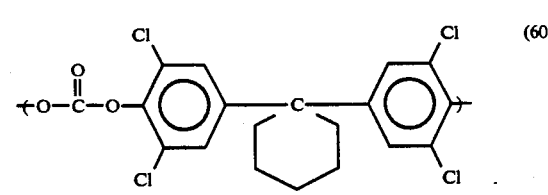

The number average molecular weight of these polycarbonate Z resins is preferably 5,000 to 100,000. If the molecular weight is below this range, no satisfactory mechanical strength is obtained, and abrasion resistance cannot be obtained. If the molecular weight exceeds 100,000, the viscosity becomes too high upon coating to ensure good workability. The glass transition point is 50° C. to 200° C., between which range improved abrasion resistance is obtained. If the glass transition point is below this range, undesirable degradation occurs in environmental properties. If the glass transition point exceeds 200° C., brittleness occurs and abrasive deterioration becomes severe.

The amount of binder used is 0.1 to 3 parts by weight per each part of the silicon-containing triarylamine compound of the present invention, preferably 0.1 to 2 parts by weight. If the binder amount exceeds this range, the charge transport material concentration in the charge transport layer decreases and the sensitivity lowers.

Also, in the present invention, the known charge transport materials described above can be used in combination where necessary.

Any coating means can be used to coat the charge transport layer with no limitation. Examples of usable means include dip coater, bar coater, calender coater, gravure coater and spin coater, and electrodeposition coating is also possible.

The thickness of the charge transport layer thus formed is preferably 10 to 50 μm, more preferably 10 to 30 μm. If the thickness exceeds 50 μm, more time is required for charge transport, and the possibility of charge trapping increases, which may cause sensitivity reduction. If the thickness is below 10 μm, the mechanical strength decreases and the life time of the photoreceptor shortens.

A photoreceptor for electrophotography incorporating a silicon-containing triarylamine compound of the present invention in its charge transport layer can be prepared as described above. Furthermore, an undercoat layer, an adhesion layer, a barrier layer, etc. can be formed as needed between the conductive substrate and the charge generation layer. Such layers can be prepared with any one of insulating resin such as polyvinyl butyral, phenol resin or polyamide resin, a dispersion of conductive inorganic fine powder in insulating resin, and conductive polymer prepared by ion doping into a conjugate polymer such as polypyrrole or polythiophene. Also, a surface protective layer may be formed on the surface of the photoreceptor, which can be made of the same material as with the undercoat layer, etc. described above.

In the use of the photoreceptor for electrophotography thus obtained, the surface of the photoreceptor is first negatively charged using a corona charger or the like. Exposure to light, which follows charging, causes the charge generation layer to generate charge pair (positive charge and negative charge). Positive charge is injected into the charge transport layer, through which it is transported to the surface of the photoreceptor, where the surface negative charge is neutralized. On the other hand, a negative charge remains unneutralized in the unexposed portion. In the case of ordinary development, a positively charging toner is used, and it adheres to this portion where the negative charge remains unneutralized and is developed thereon. In the case of reversal development, a negatively charging toner is used, and it adheres to the charge-neutralized potion and is developed thereon. The photoreceptor for electrophotography according to the present invention can be used for any development process, providing high image quality.

In the present invention, it is also possible to prepare a photoreceptor for electrophotography by forming a charge transport layer on a conductive substrate in advance and then forming a charge generation layer thereon. In this case, the surface of the photoreceptor is first positively charged and exposure to light, whereafter the resulting negative charge neutralizes the surface charge of the photoreceptor, while the positive charge is transported to the conductive substrate through the charge transport layer.

It is also possible to prepare the photoreceptor as a single-layer photoreceptor wherein a charge generation material and a charge transport material are contained in the same layer. In this case, the charge generation material and the charge transport material are dispersed and dissolved in the presence of a binder and the resulting dispersion is coated on the substrate to a film thickness of 10 to 30 μm.

EXAMPLES

The present invention is hereinafter described in more detail by means of the following examples, but the invention is not by any means limited to these examples.

EXAMPLE 1

Synsthesis of bis(4-diphenylaminophenyl)dimethylsilane (Example Compound (5))

6.5 g (20 mmol) of 4-bromotriphenylamine was placed in a 200-ml four-necked flask equipped with a mechanical stirrer, a condenser, a nitrogen-inlet tube and a dropping funnel, and the inside atmosphere was replaced with nitrogen. 100 ml of diethyl ether was added and the 4-bromotriphenylamine was dissolved therein. To this ether solution, 12.5 ml of n-butyl lithium (1.6M hexane solution, 20 mmol) was gradually added dropwise at room temperature. After completion of the addition, the mixture was stirred at room temperature for 1 hour. Then, to this reaction mixture, 20 ml of a diethyl ether solution of 1.3 g (10 mmol) of dichlorodimethylsilane was gradually added dropwise under reflux conditions. After completion of the addition, the reaction mixture was stirred for 2 hours under reflux conditions. Then, the mixture was cooled on ice water bath, and 50 ml of water was added for hydrolysis. The ether layer was extracted and washed with a saturated aqueous solution of sodium hydrogen carbonate and then with two portions of water, followed by drying with anhydrous sodium sulfate. After drying, the diethyl ether was distilled off to yield a white solid, which was then recrystallized with n-hexane/toluene (1/1) to yield 3.5 g of the desired product (yield 67%). m.p.: 170.0°–172.0° C.

| | elementary analysis: ($C_{38}H_{34}N_2Si$) | |
|---|---|---|
| | Calculated (%) | Found (%) |
| C | 83.52 | 83.26 |
| H | 6.23 | 6.42 |
| N | 5.13 | 5.33 |
| Si | 5.12 | 4.99 |

EXAMPLE 2

Synthesis of bis(4-diphenylaminophenyl)diethylsilane (Example Compound (6))

0.6 g (24.9 mmol) of metallic magnesium was placed in a 200-ml four-necked flask equipped with a mechanical stirrer, a condenser, a nitrogen-inlet tube and a dropping funnel, and the inside atmosphere was replaced with nitrogen. 100 ml of diethyl ether was added and stirring was initiated. To this solution, 20 ml of a diethyl ether solution of 6.5 g (20 mmol) of 4-bromotriphenylamine was gradually added dropwise. When about 5 ml was added, mild reflux began. Under reflux conditions, the remainder of the diethyl ether solution was added. After completion of the addition, reflux was continued for 1 more hour. The Grignard solution thus obtained was cooled to room temperature, and then 20 ml of a diethyl ether solution of 1.6 g (10 mmol) of dichlorodiethylsilane was gradually added dropwise under reflux conditions. After completion of the addition, the reaction mixture was stirred under reflux conditions for 2 hours. Then, 50 ml of water was added for hydrolysis. The ether layer was extracted and washed with a saturated aqueous solution of sodium hydrogen carbonate and then with two portions of water, followed by drying with anhydrous sodium sulfate. After drying, the diethyl ether was distilled off to yield a white solid, which was then recrystallized with n-hexane/toluene (1/1) to yield 7.8 g of the desired product (yield 70%). m.p.: 153.5°–155.0° C.

| elementary analysis: (C₄₀H₃₈N₂Si) | | |
|---|---|---|
|  | Calculated (%) | Found (%) |
| C | 83.62 | 83.39 |
| H | 6.62 | 6.74 |
| N | 4.88 | 5.19 |
| Si | 4.88 | 4.68 |

EXAMPLE 3

Synthesis of tris(4-diphenylaminophenyl)ethylsilane (Example Compound (30))

6.5 g (20 mmol) of 4-bromotriphenylamine was placed in a 200-ml four-necked flask equipped with a mechanical stirrer, a condenser, a nitrogen-inlet tube and a dropping funnel, and the inside atmosphere was replaced with nitrogen. 100 ml of diethyl ether was added and the 4-bromotriphenylamine was dissolved therein. To this ether solution, 12.5 ml of n-butyl lithium (1.6M hexane solution, 20 mmol) was gradually added dropwise at room temperature. After completion of the addition, the mixture was stirred at room temperature for 1 hour. Then, to this reaction mixture, 20 ml of a diethyl ether solution of 1.1 g (6.6 mmol) of trichloroethylsilane was gradually added dropwise under reflux conditions. After completion of the addition, the reaction mixture was stirred for 2 hours under reflux conditions. Then, the mixture was cooled on ice water bath, and 50 ml of water was added for hydrolysis. The ether layer was extracted and washed with a saturated aqueous solution of sodium hydrogen carbonate and then with two portions of water, followed by drying with anhydrous sodium sulfate. After drying, the diethyl ether was distilled off to yield a white solid, which was then recrystallized with n-hexane/toluene (1/1) to yield 3.8 g of the desired product (yield 73%).
m.p.: 235.0°–237.0° C.

| elementary analysis: (C₅₆H₄₇N₃Si) | | |
|---|---|---|
|  | Calculated (%) | Found (%) |
| C | 85.17 | 85.42 |
| H | 6.00 | 5.82 |
| N | 5.32 | 5.22 |
| Si | 3.56 | 3.54 |

EXAMPLE 4

Synthesis of tris(4-diphenylaminophenyl)n-butylsilane (Example Compound (31))

0.6 g (24.9 mmol) of metallic magnesium was placed in a 200-ml four-necked flask equipped with a mechanical stirrer, a condenser, a nitrogen-inlet tube and a dropping funnel, and the inside atmosphere was replaced with nitrogen. 100 ml of diethyl ether was added and stirring was initiated. To this solution, 20 ml of a diethyl ether solution of 6.5 g (20 mmol) of 4-bromotriphenylamine was gradually added dropwise. When about 5 ml was added, mild reflux began. Under reflux conditions, the remainder of the diethyl ether solution was added. After completion of the addition, reflux was continued for 1 more hour. The Gringnard solution thus obtained was cooled to room temperature, and then 20 ml of a diethyl ether solution of 1.3 g (6.6 mmol) of n-butyltrichlorosilane was gradually added dropwise under reflux conditions. After completion of the addition, the reaction mixture was stirred under reflux conditions for 2 hours. Then, the mixture was cooled on ice water bath, and ice cooling conditions, 50 ml of water was added for hydrolysis. The ether layer was extracted and washed with a saturated aqueous solution of sodium hydrogen carbonate and then with two portions of water, followed by drying with anhydrous sodium sulfate. After drying, the diethyl ether was distilled off to yield a white solid, which was then recrystallized with n-hexane/toluene (1/1) to yield 3.7 g of the desired product (yield 68%).
m.p.: 124.0°–127.0° C.

| elementary analysis: (C₅₈H₅₁N₃Si) | | |
|---|---|---|
|  | Calculated (%) | Found (%) |
| C | 85.19 | 84.98 |
| H | 6.24 | 6.33 |
| N | 5.14 | 5.20 |
| Si | 3.42 | 3.49 |

EXAMPLE 5

Synthesis of 4,4',4''-tris(triethylsilyl)triphenylamine (Example Compound (42))

4.0 g (8.3 mmol) of 4,4',4''-tribromotriphenylamine was placed in a 200-ml four-necked flask equipped with a mechanical stirrer a condenser, a nitrogen-inlet tube and a dropping funnel, and the inside atmosphere was replaced with nitrogen. 100 ml of diethyl ether was added and the 4,4',4''-tribromotriphenylamine was dissolved therein. To this ether solution, 16 ml of n-butyl lithium (1.6M hexane solution, 25.6 mmol) was gradually added dropwise at room temperature. After completion of the addition, the mixture was stirred at room temperature for 1 hour. Then, to this reaction mixture, 20 ml of a diethyl ether solution of 3.8 g (24.9 mmol) of triethylchlorosilane was gradually added dropwise under reflux conditions. After completion of the addition, the reaction mixture was stirred for 2 hours under reflux conditions. Then, the mixture was cooled on ice water bath, and 50 ml of water was added for hydrolysis. The ether layer was extracted and washed with a saturated aqueous solution of sodium hydrogen carbonate and then with two portions of water, followed by drying with anhydrous sodium sulfate. After drying, the diethyl ether was distilled off to yield a white solid, which was then recrystallized with n-hexane to yield 4.2 g of the desired product (yield 87%).
m.p.: 154.0°–156.0° C.

| elementary analysis: (C₃₆H₅₇NSi₃) | | |
|---|---|---|
|  | Calculated (%) | Found (%) |
| C | 73.59 | 73.10 |
| H | 9.71 | 9.87 |
| N | 2.39 | 2.25 |
| Si | 14.31 | 14.78 |

EXAMPLE 6

Synthesis of 4,4',4''-tris(trimethylsilyl)triphenylamine (Example Compound (41))

0.6 g (24.9 mmol) of metallic magnesium was placed in a 200-ml four-necked flask equipped with a mechanical stirrer, a condenser, a nitrogen-inlet tube and a dropping funnel, and the inside atmosphere was replaced with nitrogen. 100 ml of diethyl ether was added and stirring was initiated. To this solution, 20 ml of a diethyl ether solution of 4.0 g (8.3 mmol) of 4,4',4''-tribromotriphenylamine was gradually added dropwise. When about 5 ml was added, mild reflux began. Under reflux conditions, the remainder of the diethyl ether solution was added. After completion of the addition, reflux was contained for 1 more hour. The Grignard solution thus obtained was cooled to room temperature, and then 20 ml of a diethyl ether solution of 2.7 g (24.9 mmol) of trimethylchlorosilane was gradually added dropwise under reflux conditions. After completion of the addition, the reaction mixture was stirred under reflux conditions for 2 hours. Then, the mixture was cooled on ice water bath, and 50 ml of water was added for hydrolysis. The ether layer was extracted and washed with a saturated aqueous solution of sodium hydrogen carbonate and then with two portions of water, followed by drying with anhydrous sodium sulfate. After drying, the diethyl ether was distilled off to yield a white solid, which was then recrystallized with n-hexane to yield 2.8 g of the desired product (yield 74%).

m.p.: 156.0°–159.0° C.

| elementary analysis: ($C_{27}H_{39}NSi_3$) | | |
|---|---|---|
| | Calculated (%) | Found (%) |
| C | 70.28 | 70.19 |
| H | 8.46 | 8.52 |
| N | 3.04 | 3.14 |
| Si | 18.22 | 18.15 |

EXAMPLES 7 THROUGH 16

Examples Compounds (7) through (28) can be synthesized in the same manner as in Example 1 or 2. Example Compounds (29) and (32) through (40) can be synthesized in the same manner as in Example 3 or 4. Example Compounds (43) through (54) can be synthesized in the same manner as in Example 5 or 6. The yield, melting point and elementary analysis data of some of the compounds obtained by these methods are given in Table 1.

TABLE 1

| Example | Example Compound | Yield (%) | m.p. (°C.) | | Elementary Analysis (%) | | | |
|---|---|---|---|---|---|---|---|---|
| | | | | | C | H | N | Si |
| Ex. 7 | (8) | 85 | 68.5– 70.5 | Calc. Found | 83.81 83.61 | 7.30 7.54 | 4.44 4.54 | 4.45 4.31 |
| Ex. 8 | (12) | 71 | 146.0– 148.5 | Calc. Found | 85.71 85.52 | 6.29 6.65 | 4.00 4.21 | 4.00 3.62 |
| Ex. 9 | (13) | 63 | 77.0– 79.0 | Calc. Found | 84.04 84.22 | 6.84 7.02 | 4.56 4.45 | 4.56 4.31 |
| Ex. 10 | (15) | 62 | 98.0– 100.5 | Calc. Found | 83.72 83.57 | 6.98 7.12 | 4.65 4.55 | 4.65 4.76 |
| Ex. 11 | (18) | 80 | 120.5– 122.0 | Calc. Found | 83.72 83.56 | 6.98 7.19 | 4.65 4.59 | 4.65 4.66 |
| Ex. 12 | (21) | 75 | 162.5– 165.0 | Calc. Found | 84.94 84.69 | 6.63 6.98 | 4.22 4.01 | 4.21 4.32 |
| Ex. 13 | (22) | 63 | 197.5– 199.0 | Calc. Found | 85.96 85.73 | 6.02 6.08 | 4.01 4.21 | 4.01 3.98 |
| Ex. 14 | (24) | 69 | 111.0– 113.5 | Calc. Found | 83.62 83.55 | 6.62 6.69 | 4.88 5.01 | 4.88 4.75 |
| Ex. 15 | (32) | 73 | 65.5– 67.0 | Calc. Found | 85.21 85.17 | 6.51 6.66 | 4.97 5.02 | 3.31 3.15 |
| Ex. 16 | (54) | 83 | 125.2– 128.5 | Calc. Found | 76.86 76.54 | 8.88 8.97 | 2.04 2.01 | 12.22 12.48 |

EXAMPLE 17

Synthesis of polycarbonate Z resin (Example Compound (56))

100 g of 1,1-bis(4-hydroxyphenyl)cyclohexane, 50 g of sodium hydroxide, 900 g of water, 500 g of methylene chloride and 2 g of p-t-butylphenol were placed in a 2-1 four-necked flask equipped with a mechanical stirrer, a condenser and a gas-inlet tube, followed by vigorous stirring. 37 g of phosgene was bubbled at room temperature for polymerization. After completion of the polymerization, the methylene chloride layer was extracted and added dropwise to 5 l of diethyl ether for reprecipitation. The obtained white solid was filtered and dried to yield 104 g of the desired product.

The number average molecular weight of the polycarbonate Z resin thus obtained was estimated at about 50,000 as polystyrene by liquid chromatography, and its glass transition point was 141° C.

EXAMPLE 18

4.1 g of X-form metal-free phthalocyanine, 4.1 g of polyvinylbutyral (S-LEC BM-2, product of Sekisui Chemical Co., Ltd.), 200 g of cyclohexanone, and 650 g of glass beads (1 mm in diameter) were placed in a sand mill, followed by 4 hours of dissolution and dispersion to yield a coating composition for charge generation layer. This coating composition was coated on a dia-turned aluminum cylinder (30 mm in diameter) by dipping method and dried to a final film thickness of 0.15 μm.

Next, 80 g of a silicon-containing triarylamine compound represented by Example Compound (5) and 80 g of a polycarbonate Z resin (number average molecular weight=50,000) having the repeating unit represented by Example Compound (56) were dissolved in 450 g of dioxane to yield a coating composition for charge transport layer. This coating composition was coated on the aluminum cylinder which had been coated with the charge generation layer described above by dipping method to a final film thickness of 25 μm.

The drum-shaped photoreceptor for electrophotography thus prepared was evaluated as to electrophotographic properties using a drum xerography tester (electrostatic voltmeter 362A, product of Trek, Inc.; light source: semiconductor laser 790 nm). When the photoreceptor was charged with −5.5 kV corona voltage, the initial surface potential $V_0$ was found to be −880 V. After the photoreceptor was kept standing in the dark for 2 seconds, the surface potential $V_2$ became −860 V. Then, 790 nm semiconductor laser was irradiated, and the half decay exposure $E_{\frac{1}{2}}$ was found to be 0.33 μJ/cm² and the residual potential $V_R$ was −12.6 V.

Next, after the procedure described above was repeated in 50,000 cycles, the $V_0$, $V_2$, $E_{\frac{1}{2}}$ and $V_R$ were found to be −860 V, −840 V, 0.34 μJ/cm², and −14.4 V, respectively, i.e., the performance of the photoreceptor showed almost no degradation.

Next, a photoreceptor for electrophotography prepared in the same manner as above was loaded on a commercial laser beam printer of the blade cleaning and reversal development type and a print test was conducted.

Even after 50,000 copies were taken, there occurred almost no film thickness reduction, nor was there any damage which might affect image quality. Also, the obtained images maintained a high image density and had no deterioration.

The photoreceptor for electrophotography according to the present invention was thus found to be very excellent in sensitivity and durability.

EXAMPLES 19 through 25

Photoreceptors were prepared and tested for performance in the same manner as in Example 18 except that the compounds listed in Table 2 were used in place of the silicon-containing triarylamine compound represented by Example Compound (5) as the charge transport material. The results are given in Table 2.

As seen in Table 2, all the photoreceptor samples remained excellent in photoreceptor properties both in the initial stage and even after 50,000 copies were taken.

After 50,000 copies were taken with the photoreceptor loaded on the printer, no film thickness reduction occurred in any of the photoreceptors, with high image density maintained in all photoreceptors.

TABLE 2

| Example | charge transport material | | $V_0$ (V) | $V_2$ (V) | $E_{1/2}$ ($\mu J/cm^2$) | $V_R$ (V) |
|---|---|---|---|---|---|---|
| Ex. 19 | (6) | initial stage | −850 | −840 | 0.32 | −14.6 |
| | | after 50,000 copies | −840 | −830 | 0.33 | −15.6 |
| Ex. 20 | (12) | initial stage | −880 | −860 | 0.31 | −9.9 |
| | | after 50,000 copies | −870 | −850 | 0.32 | −15.3 |
| Ex. 21 | (15) | initial stage | −850 | −820 | 0.34 | −14.6 |
| | | after 50,000 copies | −820 | −790 | 0.34 | −25.1 |
| Ex. 22 | (30) | initial stage | −840 | −820 | 0.32 | −12.2 |
| | | after 50,000 copies | −820 | −800 | 0.33 | −18.3 |
| Ex. 23 | (32) | initial stage | −870 | −870 | 0.32 | −10.0 |
| | | after 50,000 copies | −840 | −820 | 0.32 | −15.8 |
| Ex. 24 | (41) | initial stage | −880 | −870 | 0.34 | −12.3 |
| | | after 50,000 copies | −860 | −830 | 0.34 | −21.0 |
| Ex. 25 | (42) | initial stage | −870 | −850 | 0.33 | −15.2 |
| | | after 50,000 copies | −860 | −840 | 0.33 | −19.0 |

EXAMPLES 26 THROUGH 28

Photoreceptors were prepared and tested for performance in the same manner as in Example 18 except that the polycarbonate Z resins listed in Table 3 were used in place of the polycarbonate Z resins having the repeating unit represented by Example Compound (56). The results are given in Table 3.

As seen in Table 3, all the photoreceptor samples remained excellent in photoreceptor properties both in the initial stage and even after 50,000 copies were taken.

After 50,000 copies were taken with the photoreceptor loaded on the printer, no film thickness reduction occurred in any of the photoreceptors, with high image density maintained in all photoreceptors.

TABLE 3

| Example | repeating unit of polycarbonate Z | | $V_0$ (V) | $V_2$ (V) | $E_{1/2}$ ($\mu J/cm^2$) | $V_R$ (V) |
|---|---|---|---|---|---|---|
| Ex. 26 | (57) | initial stage | −870 | −850 | 0.34 | −15.2 |
| | | after 50,000 copies | −840 | −820 | 0.34 | −21.3 |
| Ex. 27 | (58) | initial stage | −840 | −820 | 0.32 | −11.1 |
| | | after 50,000 copies | −820 | −800 | 0.32 | −19.8 |
| Ex. 28 | (59) | initial stage | −850 | −840 | 0.32 | −10.5 |
| | | after 50,000 copies | −820 | −780 | 0.32 | −17.0 |

EXAMPLE 29

10 g of polyamide resin (AMIRAN CM-8000, product of Toray Industries, Inc.) was dissolved in 200 g of methanol/n-butanol (2/1) to yield a coating composition for undercoat layer, which was coated on a diaturned aluminum cylinder (30 mm in diameter) by dipping method and dried to a final film thickness of 0.10 μm.

20 g of X-form metal-free phthalocyanine, 80 g of the silylated triarylamine compound represented by Example Compound (5), 80 g of a polycarbonate resin (number average molecular weight=50,000) having the repeating unit represented by Example Compound (56), 450 g of dioxane, and 650 g of glass beads (1 mm in diameter) were placed in a sand mill, followed by 4 hours of dissolution and dispersion to yield a coating composition for single layer structure. This coating composition was coated on the undercoated aluminum cylinder by dipping method to a final film thickness of 25 μm.

The drum-shaped photoreceptor for electrophotography thus prepared was evaluated as to electrophotographic properties using a drum xerography tester. When the photoreceptor was charged with −5.5 kV corona voltage, the initial surface potential $V_0$ was found to be −800 V. After the photoreceptor was kept standing in the dark for 2 seconds, the surface potential $V_2$ became −770 V. Then, 790 nm semiconductor laser was irradiated, and the half decay exposure $E_{\frac{1}{2}}$ was found to be 0.46 μJ/cm² and the residual potential $V_R$ was −25.6 V.

Next, after the procedure described above was repeated in 50,000 cycles, the $V_0$, $V_2$, $E_{\frac{1}{2}}$ and $V_R$ were found to be −780 V, −750 V, 0.47 μJ/cm², and −38.8 V, respectively, i.e., the performance of the photoreceptor showed almost no degradation.

Next, a photoreceptor for electrophotography prepared in the same manner as above was loaded on a commercial laser beam printer of the blade cleaning and reversal development type and a print test was conducted.

Even after 50,000 copies were taken, there occurred almost no film thickness reduction, nor was there any damage which might affect image quality.

The photoreceptor for electrophotography according to the present invention was thus found to be very excellent in sensitivity and durability.

EXAMPLE 30

5 g of dibromoanthanthrone and 5 g of butyral resin (S-LEC BM-2, product of Sekisui Chemical Co., Ltd.) were dispersed and dissolved in 90 ml of cyclohexanone and kneaded in a ball mill for 24 hours. The obtained dispersion was coated on an aluminum plate using a bar coater and dried to a final film thickness of 0.15 μm to yield a charge generation layer.

Next, 5 g of a silylated triphenylamine compound represented by Example Compound (5) and 5 g of a polycarbonate resin (LEXAN® 131-111, product of Engineering Plastics K.K.) were dissolved in 90 ml of dioxane. The resulting solution was coated on the charge generation layer formed in advance using a blade coater and dried to a final film thickness of 25 μm to yield a charge transport layer.

The photoreceptor for electrophotography thus prepared was charged with −5.5 kV corona voltage using the test equipment for electrostatic paper analyzer EPA-8100, produced by Kawaguchi Denki Seisakusho K.K.; the initial surface potential $V_0$ was found to be −780 V. After the photoreceptor was kept standing in the dark for 2 seconds, the surface potential $V_2$ became −770 V. Then, the photoreceptor was irradiated with a halogen lamp of a illuminance of 5 lux, and the half decay exposure $E_{\frac{1}{2}}$ was found to be 1.2 lux·sec and the residual potential $V_R$ was −12.5 V.

Next, after the procedure described above was repeated in 5,000 cycles, $V_0$, $V_2$, $E_{\frac{1}{2}}$ and $V_R$ were found to be −770 V, −770 V, 1.3 lux·sec, and −13.2 V, respectively, i.e., the photoreceptor proved to be excellent in photoreceptor performance and high durability.

EXAMPLES 31 THROUGH 38

Photoreceptors were prepared and tested for performance in the same manner as in Example 30 except that the compounds listed in Table 4 were used as charge transport materials. The results are given in Table 4.

TABLE 4

| Example | charge transport material | | $V_0$ (V) | $V_2$ (V) | $E_{1/2}$ (lux·sec) | $V_R$ (V) |
|---|---|---|---|---|---|---|
| Ex. 31 | (8) | initial stage | −780 | −770 | 1.4 | −25.3 |
| | | after 5,000 copies | −770 | −760 | 1.4 | −25.9 |
| Ex. 32 | (13) | initial stage | −780 | −770 | 1.3 | −15.6 |
| | | after 5,000 copies | −780 | −760 | 1.4 | −16.1 |
| Ex. 33 | (18) | initial stage | −760 | −750 | 1.3 | −10.2 |
| | | after 5,000 copies | −750 | −730 | 1.4 | −13.3 |
| Ex. 34 | (21) | initial stage | −810 | −780 | 1.5 | −18.0 |
| | | after 5,000 copies | −800 | −780 | 1.5 | −21.0 |
| Ex. 35 | (24) | initial stage | −800 | −790 | 1.2 | −10.2 |
| | | after 5,000 copies | −780 | −770 | 1.2 | −12.2 |
| Ex. 36 | (30) | initial stage | −780 | −770 | 1.0 | −10.5 |
| | | after 5,000 copies | −780 | −770 | 1.1 | −12.9 |
| Ex. 37 | (42) | initial stage | −810 | −790 | 1.2 | −11.5 |
| | | after 5,000 copies | −780 | −770 | 1.2 | −13.7 |
| Ex. 38 | (54) | initial stage | −790 | −780 | 1.2 | −11.4 |
| | | after 5,000 copies | −780 | −770 | 1.2 | −12.9 |

COMPARATIVE EXAMPLE 1

A photoreceptor was prepared and tested for performance in the same manner as in Example 18 except that 4,4′,4″-trimethyltriphenylamine was used in place of Example Compound (5) as the charge transport material.

When the photoreceptor was charged with −5.5 kV corona voltage, the initial surface potential $V_0$ was found to be −880 V. After the photoreceptor was kept standing in the dark for 2 seconds, the surface potential $V_2$ became −860 V. Then, 790 nm semiconductor laser was irradiated, and the half decay exposure $E_{\frac{1}{2}}$ was found to be 0.89 μJ/cm² and the residual potential $V_R$ was −42.6 V.

Next, after the procedure described above was repeated in 50,000 cycles, the $V_0$, $V_2$, $E_{\frac{1}{2}}$ and $V_R$ were found to be −860 V, −820 V, 0.94 μJ/cm² and −63.1 V, respectively, i.e., the performance of the photoreceptor was worse than that of example 18.

Next, a photoreceptor for electrophotography prepared in the same manner as above was loaded on a commercial laser beam printer of the blade cleaning and reversal development type and a print test was conducted. Even after 50,000 copies were taken, there occurred almost no film thickness reduction, nor was there any damage which might affect image quality. But, the obtained images showed a low image density due to low sensitivity.

COMPARATIVE EXAMPLE 2

Synthesis of 4-triethylsilyltriphenylamine 8.1 g (24.9 mmol) of 4-bromotriphenylamine was placed in a 200-ml four-necked flask equipped with a mechanical stirrer, a condenser, a nitrogen-inlet tube and a dropping funnel, and the inside atmosphere was replaced with nitrogen. 100 ml of diethyl ether was added and the 4-bromotriphenylamine was dissolved therein. To this ether solution, 16 ml of n-butyl lithium (1.6M hexane solution, 25.6 mmol) was gradually added dropwise at room temperature. After completion of the addition, the mixture was stirred at room temperature for 1 hour. Then, to this reaction mixture, 20 ml of a diethyl ether solution of 3.8 g (24.9 mmol) of triethylchlorosilane was gradually added dropwise under reflux conditions. After completion of the addition, the reaction mixture was stirred for 2 hours under reflux conditions. Then, under ice cooling conditions, 50 ml of water was added for hydrolysis. The ether layer was extracted and washed with a saturated aqueous solution of sodium hydrogen carbonate and then with two portions of water, followed by drying with anhydrous sodium sulfate. After drying, the diethyl ether was distilled off to yield a white liquid, which was then distilled to yield 6.5 g of the desired product (yield 73%).

b.p.: 187°-191° C. (0.3 mmHg)

Next, a photoreceptor was prepared and tested for performance in the same manner as in the Example 18 except that 4-triethylsilyltriphenylamine was used in place of Example Compound (5) as the charge transport material.

When the photoreceptor was charged with −5.5 kV corona voltage, the initial surface potential $V_0$ was found to be −890 V. After the photoreceptor was kept standing in the dark for 2 seconds, the surface potential $V_2$ became −880 V. Then, a semiconductor laser of an oscillating wavelength of 790 nm was irradiated, and the half decay exposure $E_{\frac{1}{2}}$ was found to be 1.97 μJ/cm² and the residual potential $V_R$ was −315 V. Next, after the procedure described above was repeated in 50,000 cycles, the $V_0$, $V_2$, $E_{\frac{1}{2}}$ and $V_R$ were found to be −1100 V, −1070 V, 3.88 μJ/cm² and −433 V, respectively, i.e., the performance of the photoreceptor was worse than that of example 18.

Next, a photoreceptor for electrophotography prepared in the same manner as above was loaded on a commercial laser beam printer of the blade cleaning and reversal development type and a print test was conducted. The obtained images showed a considerable low image density due to low sensitivity, and the surface of the photoreceptor for electrophotography thus prepared was adhesive and also the cleaning of toner worsened since 4-triethylsilyltriphenylamine was liquid.

What is claimed is:

1. A compound represented by the formula (1):

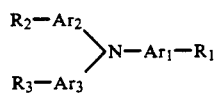  (1)

wherein $Ar_1$ represents an arylene group; $Ar_2$ and $Ar_3$ independently represent an aryl group or an arylene group; $R_2$ and $R_3$, which may be identical or different, independently represent a hydrogen atom or an alkyl group having a carbon number of 4 or less, or $R_2$ and $R_3$ both represent $-SiR_4R_5R_6$, wherein $R_4$, $R_5$, and $R_6$, which may be identical or different, independently represent an alkyl group, a substituted or unsubstituted aralkyl group or a substituted or unsubstituted aryl group;

$R_1$ represents $-SiR_7R_8R_9$ wherein $R_7$, $R_8$, and $R_9$, which may be identical or different, independently represent an alkyl group, a cycloalkyl group, a substituted or unsubstituted aralkyl group or a substituted or unsubstituted aryl group and up to two of $R_7$, $R_8$, and $R_9$ represent the following:

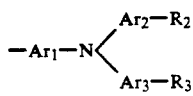

wherein $Ar_1$, $Ar_2$, $Ar_3$, $R_2$ and $R_3$ have the same definitions as above with the proviso that when both $R_2$ and $R_3$ are not $-SiR_4R_5R_6$, one or two of $R_7$, $R_8$ and $R_9$ represent the following:

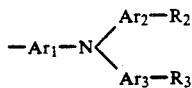

wherein $Ar_1$, $Ar_2$, $Ar_3$, $R_2$ and $R_3$ have the same definitions as above.

2. A compound according to claim 1 of the formula (2):

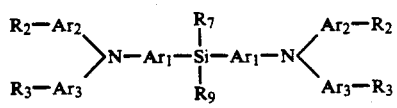  (2)

wherein $Ar_1$, $Ar_2$, $Ar_3$, $R_2$, $R_3$, $R_7$ and $R_9$ have the same definitions as claim 1.

3. A compound according to claim 2 wherein $R_7$ and $R_9$ represent alkyl groups.

4. The compound according to claim 2 of the formula:

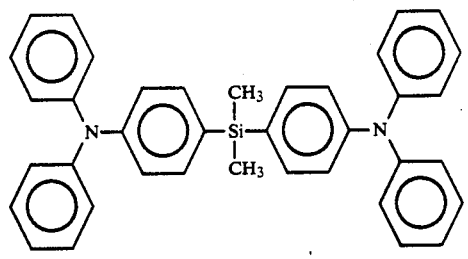

5. The compound according to claim 2 of the formula:

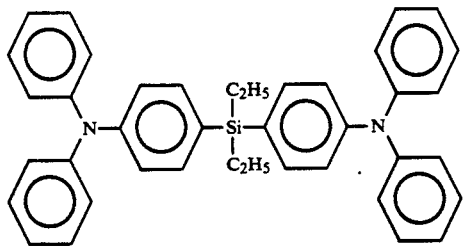

6. A compound according to claim 1 of the formula (3):

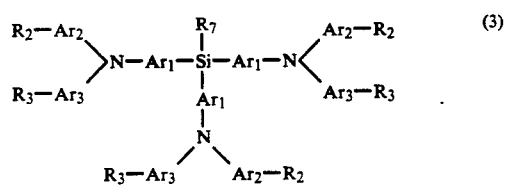  (3)

wherein $Ar_1$, $Ar_2$, $Ar_3$, $R_2$, $R_3$ and $R_7$ have the same definitions as claim 1.

7. A compound according to claim 6 wherein $R_7$ represents an alkyl group.

8. The compound according to claim 6 of the formula:

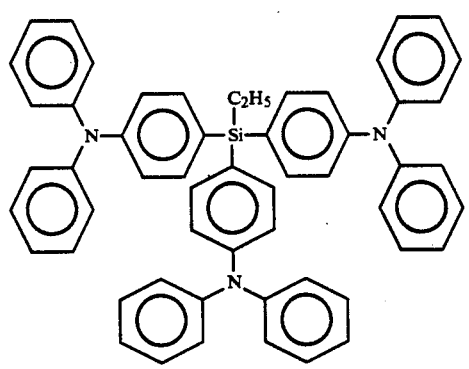

9. The compound according to claim 6 of the formula:

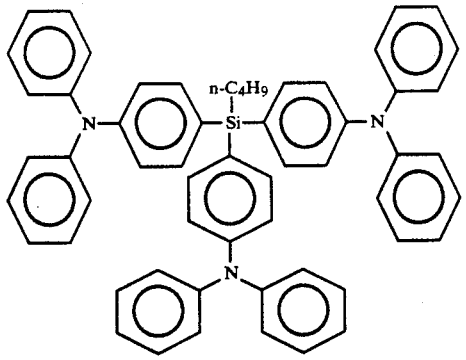

10. A compound according to claim 1 of the formula (4):

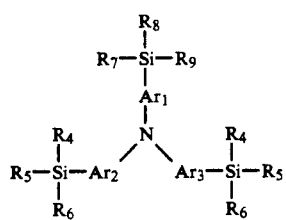

wherein $Ar_1$, $Ar_2$, $Ar_3$, $R_4$, $R_5$, $R_6$, $R_7$, $R_8$ and $R_9$ have the same definitions as claim 1.

11. A compound according to claim 10 wherein $R_4$, $R_5$, $R_6$, $R_7$, $R_8$ and $R_9$ represent alkyl groups.

12. The compound according to claim 10 of the formula:

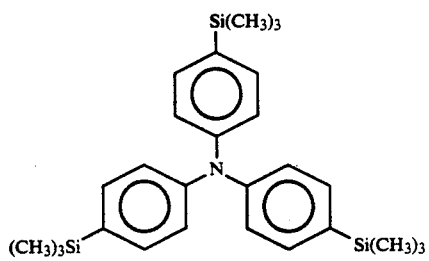

13. The compound according to claim 10 of the formula:

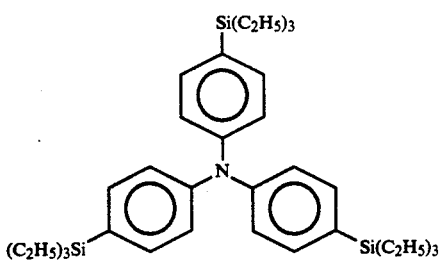

14. A method for producing a compound of claim 1 which comprises reacting a lithium reagent derived from a halogenated triarylamine compound represented by the formula (1)':

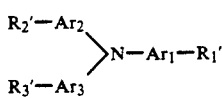

wherein $Ar_1$, $Ar_2$, and $Ar_3$ have the same definitions as claim 1; one or all of $R_1'$, $R_2'$ and $R_3'$ are halogen atoms; if they are not halogen atoms, $R_1'$ has the same definition as $R_1$, $R_2'$ has the same definition as $R_2$, and $R_3'$ has the same definition as $R_3$, and a silane compound represented by $X_1SiR_7'R_8'R_9'$ wherein $X_1$ represents a halogen atom, a methoxy group, or an ethoxy group; up to two of $R_7'$, $R_8'$ and $R_9'$ independently represent a halogen atom, a methoxy group, or an ethoxy group while the remaining one, two or three, which may be identical or different, independently represent an alkyl group, cycloalkyl group, substituted or unsubstituted aralkyl group or substituted or unsubstituted aryl group.

15. A method according to claim 14 which comprises lithionating a halogenated triarylamine compound when only $R_1'$ of the formula (1)' is a halogen atom with an organic lithium reagent, and then reacting said lithionated compound with a silane compound represented by $X_1SiX_1R_8'R_9'$ wherein $X_1$ represents a halogen atom, a methoxy group or an ethoxy group, and $R_8'$ and $R_9'$, which may be identical or different, independently represent an alkyl group, cycloalkyl group, substituted or unsubstituted aralkyl group or substituted or unsubstituted aryl group.

16. A method according to claim 14 which comprises lithionating a halogenated triarylamine compound when only $R_1'$ of the formula (1)' is a halogen atom with an organic lithium reagent, and then reacting said lithionated compound with a silane compound represented by $X_1SiX_1X_1R_9'$ wherein $X_1$ represents a halogen atom, a methoxy group or an ethoxy group, and $R_9'$ represents an alkyl group, cycloalkyl group, substituted or unsubstituted aralkyl group or substituted or unsubstituted aryl group.

17. A method according to claim 14 which comprises lithionating a halogenated triarylamine compound when $R1'$, $R_2'$ and $R_3'$ of the formula (1)' are halogen atoms with an organic lithium reagent, and then reacting said lithionated compound with a silane compound represented by $X_1SiR_7'R_8'R_9'$ wherein $X_1$ represents a halogen atom, a methoxy group or an ethoxy group, and $R_7'$, $R_8'$ and $R_9'$, which may be identical or not, independently represent an alkyl group, cycloalkyl group, substituted or unsubstituted aralkyl group or substituted or unsubstituted aryl group.

18. A method for producing a compound of claim 1 which comprises reacting a Grignard Reagent derived from a halogenated triarylamine compound represented by the formula (1)':

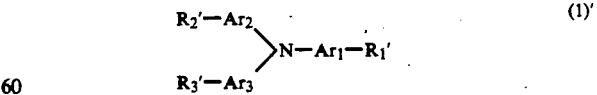

wherein $Ar_1$, $Ar_2$ and $Ar_3$ have the same definitions as claim 1; one or all of $R_1'$, $R_2'$ and $R_3'$ are halogen atoms; if they are not halogen atoms, $R_1'$ has the same definition as $R_1'$, $R_2'$ has the same definition as $R_2$, and $R_3'$ has the same definition as $R_3$, and a silane compound represented by $X_1SiR_7'R_8'R_9'$ wherein $X_1$ represents a halogen atom, a methoxy group, or an ethoxy group; up two of $R_7'$, $R_8'$ and $R_9'$ independently represent a halogen atom, a methoxy group, or an ethoxy group while the remaining one, two or three, which may be identical or not, independently represent an alkyl group, cycloalkyl group, substituted or unsubstituted aralkyl group or substituted or unsubstituted aryl group.

19. A method according to claim 18 which comprises reacting a halogenated triarylamine compound when only $R_1'$ of the formula (1)' is a halogen atom with metallic magnesium, and then reacting said Grignard reagent with a silane compound represented by $X_1SiX_1R_8'R_9'$ wherein $X_1$ represents a halogen atom, a methoxy group or an ethoxy group, and $R_8'$ and $R_9'$, which may be identical or different, independently represent an alkyl group, cycloalkyl group, substituted or unsubstituted aralkyl group or substituted or unsubstituted aryl group.

20. A method according to claim 18 which comprises reacting a halogenated triarylamine compound when only $R_1'$ of the formula (1)' is a halogen atom with metallic magnesium, and then reacting said Grignard reagent with a silane compound represented by $X_1SiX_1X_1'R_9'$ wherein $X_1$ represents a halogen atom, a methoxy group or an ethoxy group, and $R_9'$ represents an alkyl group, cycloalkyl group, substituted or unsubstituted aralkyl group or substituted or unsubstituted aryl group.

21. A method according to claim 18 which comprises reacting a halogenated triarylamine compound when only $R_1'$, $R_2'$ and $R_3'$ of the formula (1)' are halogen atoms with metallic magnesium, and then reacting said Grignard reagent with a silane compound represented by $X_1SiR_7'R_8'R_9'$ wherein $X_1$ represents a halogen atom, a methoxy group or an ethoxy group, and $R_7'$, $R_8'$ and $R_9'$, which may be identical or different, independently represent an alkyl group, cycloalkyl group, substituted or unsubstituted aralkyl group or substituted or unsubstituted aryl group.

* * * * *